United States Patent
Bullis

(10) Patent No.: US 6,976,962 B2
(45) Date of Patent: Dec. 20, 2005

(54) ENHANCED FOCUSING OF PROPAGATING WAVES BY COMPENSATION FOR MEDIUM ATTENUATION

(76) Inventor: James K. Bullis, 1155 Pimento Ave., Sunnyvale, CA (US) 94087

( * ) Notice: Subject to any disclaimer, the term of this patent is extended or adjusted under 35 U.S.C. 154(b) by 634 days.

(21) Appl. No.: 09/975,033

(22) Filed: Oct. 10, 2001

(65) Prior Publication Data

US 2003/0069500 A1 Apr. 10, 2003

(51) Int. Cl.$^7$ ................................................. A61B 8/00
(52) U.S. Cl. ..................................................... 600/459
(58) Field of Search ........................ 600/437, 442–443, 600/459, 449; 73/599, 644, 597; 601/2

(56) References Cited

U.S. PATENT DOCUMENTS

| | | | |
|---|---|---|---|
| 567,372 A | * | 9/1896 | Beaon ........................ 99/569 |
| 5,902,748 A | | 5/1999 | Madsen et al. |
| 6,013,031 A | * | 1/2000 | Mendlein et al. ........... 600/442 |
| 6,077,224 A | * | 6/2000 | Lang et al. .................. 600/437 |
| 6,485,420 B1 | * | 11/2002 | Bullis .......................... 600/437 |

OTHER PUBLICATIONS

Moshfeghi et al. In vivo and in vitro Ultrasound Beam Distortion Measurements of a Large Aperture and a Conventional Aperture Focused Transducer.

* cited by examiner

Primary Examiner—Francis J. Jaworski

(57) ABSTRACT

Improved focusing of waves is accomplished by compensation for attenuation effects in a medium. The invention is a combination of a method of attenuation leveling to allow operation over uneven surfaces and a method of signal compensation for attenuation that varies with frequency. This combination allows effective focusing of wide band wave signals that operate through irregular surfaces that cause uneven attenuation effects. Apparatus is provided to implement this method in clinical applications and research applications. Spatial attenuation leveling is accomplished with material that attenuates like the body part to be imaged. Compensation for attenuation that varies with frequency is provided by electronic modification of signal waveforms. Applications in the field of ultrasonic imaging in human tissue are specifically discussed. The apparatus includes conformal surfaces that are in contact with a patient's body that serve to prevent direct contact of the body with the attenuating material. It also includes fairing surfaces that modify shape of a patient's body to enable scanning of surfaces. Alternate devices include stand-off devices and immersion configurations.

36 Claims, 4 Drawing Sheets

ENHANCED FOCUSING OF PROPAGATING WAVES BY COMPENSATION FOR MEDIUM ATTENUATION

BACKGROUND OF THE INVENTION

1. Field of the Invention

Figure 1:
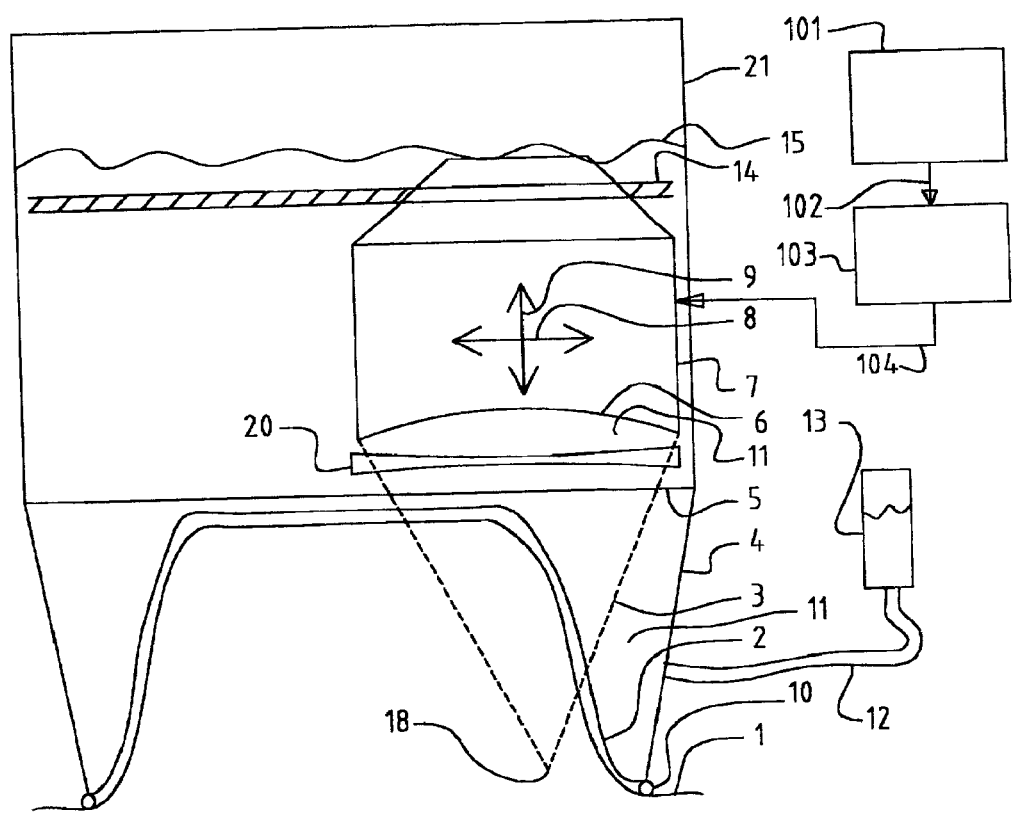

The invention relates to creating images by transmitting signals and sensing the effect of objects in the field of view on the signals.

2. Description of the Prior Art

Ultrasonic, or ultrasound, imaging devices depend on signal wavefronts that propagate into the body. A wavefront can be described by connecting points of equal phase at a given point in time to form a surface that is perpendicular to the direction that ray paths propagate. The wavefront emanates from a transducer aperture and is shaped by a combination of the transducer surface shape and phasing of signals from separate elements of the transducer surface. For focused operation, the wavefront converges to a point, except that diffraction prevents perfect convergence. Successive wavefronts act like new sources of the signal that are ever smaller and closer to the focus point. The reverse process similarly applies to reception where signals from a point source cause a wavefront of spherical shape which is ideally received by a spherical surface receiver. The body of knowledge of wave propagation physics is relied on to refine and extend this concept.

Effective system focusing requires that signal amplitude along the wavefront be well behaved. Problems arise when attenuation is uneven for different paths such that amplitude variations occur along a wavefront. When a coupling fluid is used to allow waves to travel between a transducer and a body it often happens that uneven attenuation situations are set up. As the wavefront propagates through a medium, where the medium is a combination of coupling fluid and body tissue, different paths can undergo different attenuation processes. Undesirable deviations in amplitude can result. This can change the apparent sidelobe levels. Apparent sidelobes are the actual beam response functions that are caused by the propagation effects in combination with ideal aperture effects. Apparent sidelobes will be simply called sidelobes here. This problem is especially significant for high resolution imaging which depends on large apertures and high frequency signals.

Attenuation means the reduction in signal amplitude other than the reduction that comes from geometric spreading of waves. It is also considered separately from the opposite effect of signal level increase that coming from geometric focusing of waves.

Conventional ultrasound practice tends to involve direct contact of a transducer with the skin. Here the body tissue attenuates signals with uniformity over the ray paths to the degree that body tissue is uniform.

It is known in radio frequency antenna design to control power intensity over the antenna aperture with absorbing materials to achieve the desired radiation pattern. It is also known to taper or weight an aperture, where an aperture is a radiating surface of an array of transducers, to reduce sidelobe response.

In the frequency domain an additional complication is known. This is the fact that there is an extreme variation of attenuation with frequency, according to the rule of about 0.5 dB per centimeter per megahertz. It is known that this effect also causes degradation of focus. An experiment carried out by Moshfeghi and Waag showed that for excised liver samples, focusing beam width was greater for wide band signals than it was for narrow band signals (Moshfeghi et al., In vivo and in vitro ultrasound beam distortion measurements of a large aperture and a conventional aperture focused transducer).

It is known in ultrasound clinical practice to couple ultrasound signals from transducers to the body by use of a water stand-off. Hitachi Part Number EZU-WL1 is a water bag attachment where the water volume can be adjusted by a syringe. There is a danger with such water filled accessories because the signals at a focus point are not attenuated for shallow operation as they are naturally for deep operation. Although the power levels can be adjusted, it is an action that could be easily forgotten.

Another accessory for oblique stand-off is Hitachi part number EUP-L53ST which is also water filled.

The disclosure of U.S. Pat. No. 5,902,748 (May 1999) Madsen et al. describes a water bag to couple ultrasonic signals from a transducer to a phantom where the phantom mimicks tissue. This method couples the maximum power to the focal point but may not satisfactorily control sidelobe response for a variety of phantom shapes.

It is also known to use a tank or bath wherein a fluid couples signals between a transducer and a subject of examination. A coupling fluid means that the fluid serves as an ultrasonic transmitting medium. Water is commonly used as the fluid but a variety of other fluids are used to enable signal coupling. Castor oil is known to match fat for speed of propagation, thus preventing refraction at a boundary. Johnson and Johnson baby oil is also known as a good match for breast tissue. Like water stand-offs in clinical practice, this method couples the maximum amount of power intensity to the focal point but it may not necessarily produce the desired control of sidelobe response.

It is known to produce tissue mimicking materials for use in forming ultrasound phantoms. U.S. Pat. No. 5,902,748 (May 1999) Madsen et al. discloses useful recipes for making materials that attenuate and propagate as necessary to represent human body parts. This material is specified to be adjustable to match in detail over a wide bandwidth of frequencies.

It is known in manufacturing of composite materials to vacuum bag an assembly to remove air bubbles and cause flexible surfaces to mutually conform to each other.

Subjects of examination by ultrasound are commonly human or animal. Other uses are known in other fields.

Referenced documents, in entirety, are incorporated herein. They contribute to the description of the present invention, but in case of conflict, the present document takes precedence.

OBJECTS

A general object is to realize maximum resolution benefits of large aperture, high frequency, wide bandwidth, ultrasonic imaging apparatus by utilizing a combination of an attenuation leveling method and a frequency dependent attenuation compensation method. This method provides controlled attenuation over propagation paths so that signals are at desired amplitudes over wavefronts. This would be able to accommodate different human tissue types. The same applies to animal tissue.

An object is to provide a signal transmission method that is generally useful in clinical practice or laboratory experimental procedure.

An object is to provide safety in ultrasound imaging without causing undue reduction in level of transmitted signals from transducers.

An object is to provide flexible surfaces that comfortably conform to body parts.

An object is to provide shallow viewing near the skin surface.

An object is to establish a fairing surface that enables effective scanning by transducer motion.

An object is to establish a fairing surface that simplifies control of signal amplitudes that are transmitted from various transducer elements.

An object is to establish a fairing surface that shapes body parts to an acceptable degree so as to enable variations between subjects to be accommodated.

An object is to enable treatment access simultaneously with real time imaging.

An object is to establish a laboratory method where uniform wavefronts are maintained by using attenuating material to fill in paths between body parts and transducers.

An object is to provide pre-compensation to balance attenuation variations over different paths and frequencies.

An object is to enable sidelobe control using tapered or weighted amplitude distribution functions.

An object is to combine attenuation compensation with lens functions.

An object is to utilize these methods in industrial inspection and other fields that involve wave front propagation.

Further objects of the present invention will become apparent from a consideration of the drawings and ensuing description.

SUMMARY OF THE INVENTION

The invented method involves use of attenuating fluid to maintain a desired amplitude distribution over the surface of a signal wavefront as the wavefront travels between a transducer and a point that is in human tissue and use of compensated signals to cause received signals to have a desired amplitude distribution over the frequency spectrum that describes the received signals. This method further involves a fairing surface, a conformal surface, and special coupling fluid in an arrangement that is devised to convert a human body surface into a surface that is more amenable to high quality ultrasound imaging.

DRAWINGS

FIG. 1—an apparatus to compensate for tissue attenuation effects.

Figure 2:
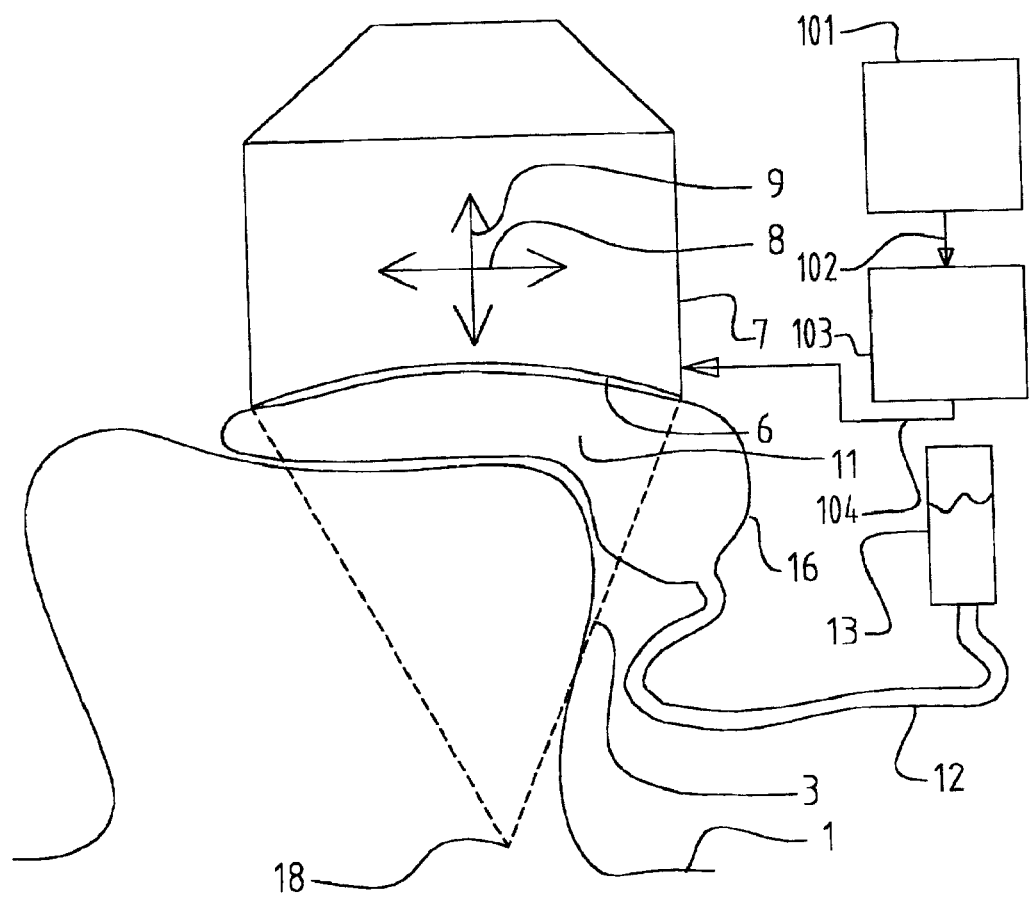

FIG. 2—an attenuating safety stand-off with reservoir to maintain attenuation fluid in stand-off pouch.

Figure 3:
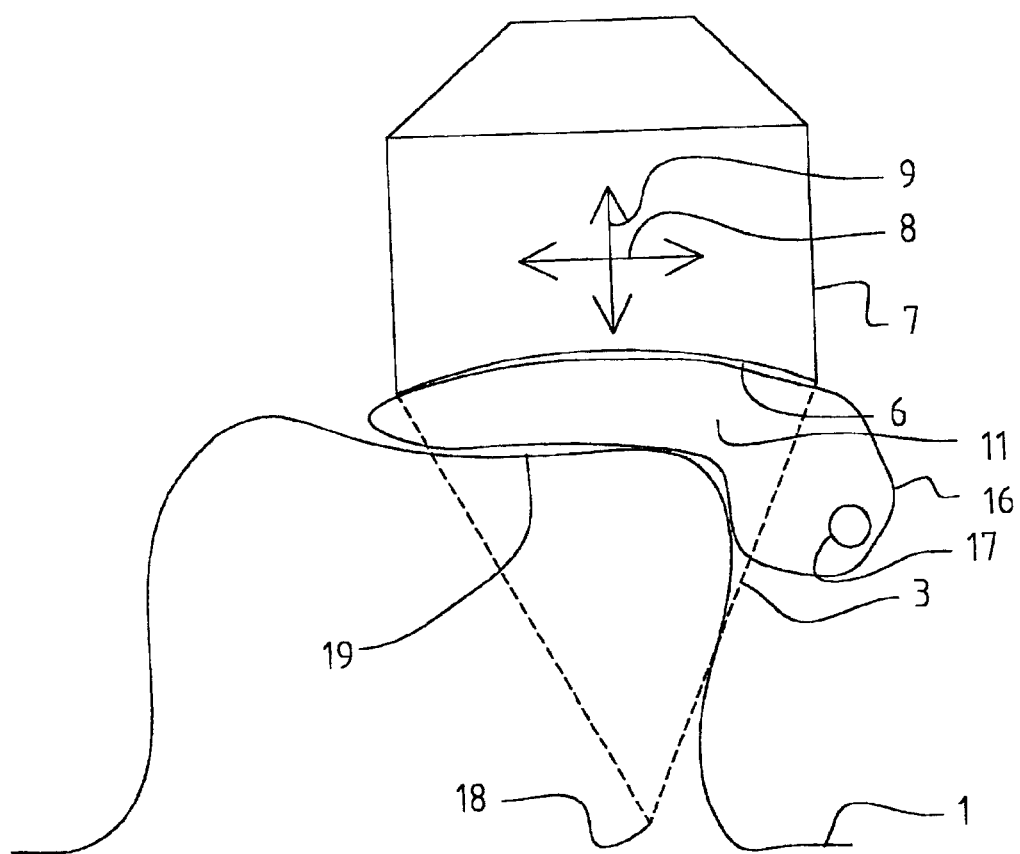

FIG. 3—an attenuating safety stand-off with capability to be filled by syringe.

Figure 4:
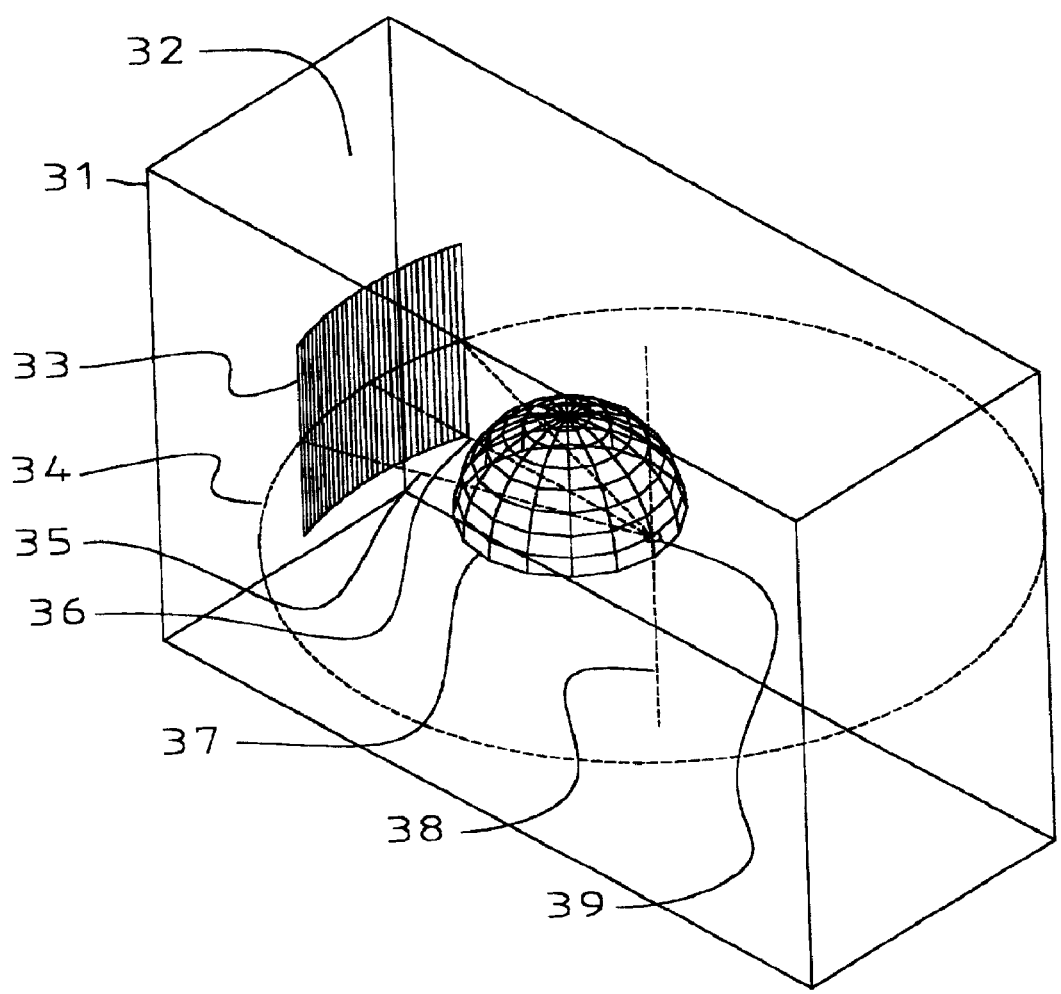

FIG. 4—an experiment set-up with a tissue mimicking phantom in a tank.

DESCRIPTION OF THE PREFERRED EMBODIMENT

The scope of the invention should be determined by the appended claims and their legal equivalents and not by the examples and variations given. Actual medical practice would be expected to result in many variations of this concept.

This invention involves an interface that can be described as a drum where one end of the drum has a thin rubber sheet fastened to one end of the cylindrical shell of the drum. The other end of the drum has a sheet of Mylar drawn tightly over the other end. The cylindrical shell of the drum is actually a tapered cylinder, that is, a hollow cone. This forms a container that is filled with attenuating fluid that attenuates at the same rate per cm per MHz. as does the body part that is to be examined. Using predictions of this rate, signals are generated that emphasize the frequency spectrum to balance the attenuation effects such that after reception, the intended level spectrum occurs. The rubber sheet conforms to the body part. The Mylar sheet remains planar. A transducer operating outside the drum through the Mylar sheet will produce the same signal amplitude at the focus point regardless of its lateral position. A coupling fluid efficiently transfers signals from the transducer to the Mylar sheet surface. This would be in a container formed on the opposite side of the Mylar sheet. Better control of the wavefront will be achieved by making this coupling fluid an attenuating coupling fluid. This will give a capability to move the transducer axially while still maintaining the same power intensity at the focus point and maintaining the quality of the focus.

Detailed features include a vacuum method to improve adherence and coupling between human skin surfaces and the rubber sheet and fluid pressure control. Both the Mylar and the rubber sheet are thin such that they have no effect on signal propagation.

An immediate system application involves a transducer that is mechanically scanned. This system enables breast imaging where a variety of breast sizes and shapes can be accommodated. Mechanical scanning is facilitated by the fairing surface formed by the taut Mylar sheet.

Another variation is a pre-compensating attenuating pad that allows for variations in the fluid in which the transducer is immersed. Pre-compensation is an uneven way to control attenuation because wavefronts are allowed to be uneven in amplitude over different successive positions and this can give rise to scattering effects.

Variations include use of conventional, hand held ultrasound transducers with fluid filled cushions that are thin walled, rubber pouches that are filled from a reservoir or with a syringe. In such cases, the fluid is an attenuating fluid such as evaporated milk. Fluids vary to suit the applicable tissue type. Fluids can be gels or other firm or solid materials as desired.

Safety is improved over conventional water stand-off methods since the power level transmitted can be kept at the maximum level needed for deep penetration.

Other variations exclude the fairing function. These include a fluid bath wherein both a transducer and a subject of examination are immersed and the fluid is an attenuating fluid that enables uniform amplitude wavefront.

The invented method provides the process of leveling the effects of attenuation on wavefronts. From a radiating surface 6 indicated in FIG. 1 to a focus point 18 in the same FIG. 1 a set of many, evenly distributed paths can be drawn that are called ray paths. The method is to insert materials that may be solid or liquid in way of such ray paths so as to cause uniform attenuation over all such ray paths. Certain tapering of attenuation is also appropriate. The simplest way to insert such material is to allow an attenuating fluid to fill in uneven body terrain where the attenuating fluid is matched in attenuation to the body attenuation. FIG. 1 also indicates a set of arbitrary waveform generators 101 that produce signals 102 with a device to modify signals 103 to produce pre-compensated signals 104 that are spectrum modified signals. An arbitrary waveform generator is a digital memory based device that contains signal samples that are formed by applying a Fourier analysis to an intended, ideal signal to determine frequency components that are samples of the waveform in the frequency domain. These samples are then modified according to a function that is the opposite of attenuation. An inverse Fourier analysis of the modified signals then yields a time domain signal that balances the attenuation effects of the medium of propagation. These are preparatory steps that are done in advance of actual operation. In actual operation, samples of the time domain signals are then transmitted in bursts by arbitrary waveform generators, as necessary to arrange all the time adjusted signals for transmit beamforming.

A combination of a fairing surface, a conformal surface, and special coupling fluid is devised to convert a human body surface into a surface that is more amenable to high quality ultrasound imaging, with an added benefit of safety. In some forms, the fairing surface is established with a stiff barrier surface. In the simpler forms, the fairing surface is established by the shape of the transducer face in contact with a flexible membrane. The special fluid couples energy between body and transducer as well as matches the attenuation of human tissue. This is useful where the body surface is uneven or an angle not perpendicular to the skin is desired. It also allows more freedom of movement in searching and optimizing an image, though contact with the stand-off device needs to be maintained.

The preferred embodiment is described here in reference to FIG. 1. A skin surface 1 is in close contact with a thin latex rubber sheet 2 which is sealed to a tapered container 4. Sides of tapered container 4 are tapered to accommodate large aperture illumination. The rubber sheet 2 is shown conformal to the skin 1 even though the body part is irregular as might be a female breast. A Mylar sheet 5 is taut against the opposite end of the tapered container 4. This tapered container is filled with attenuating fluid 11 such as evaporated milk. Materials would be derived from the body of knowledge, that includes recipes of U.S. Pat. No. 5,625,137 (May 1999) Madsen et al., for making ultrasound phantoms. A generic transducer 7 is immersed in a coupling fluid 22 contained in upper container 21 to a level 15, but the coupling fluid can alternatively be an attenuating fluid like the lower attenuating fluid 11. A transducer radiating surface 6 creates a wavefront that represents a wave signal that represents the transmitted signal. This wavefront propagates toward and converges at a point 18 subject to diffraction limitations. Wavefront convergence is indicated by boundary line 3 along with a like boundary on the opposite side. A pad 20 that represents an attenuating material is used for pre-compensation for coupling fluid 22 that does not attenuate, though it is not needed for coupling fluid that attenuates. The same pad 20 alternately, or in combination with an attenuation function, represents a refracting lens function that operates like curvature and time delay methods to focus beams. The generic transducer 7 moves laterally as indicated by double headed arrow 8 and axially as indicated by double headed arrow 9. A generic mechanism 14 to mechanically move the transducer is indicated without detail. A sealing device 10 stops air leakage around the skin perimeter and also transfers vacuum around that perimeter. This causes the attenuating fluid to take the shape of the body part with only the thin rubber sheet 2 as a barrier. The rubber sheet 2 is of thickness that is less than one fourth wavelength for ultrasound in that material so it is of negligible ultrasonic effect. The same rule applies to the Mylar sheet 5. Attenuating fluid 11 is allowed to freely transfer via tubing 12 between its container 4 and the reservoir 13 where the reservoir is vented at the top to atmospheric pressure.

The illustrated apparatus accomplishes the primary object of this invention because all paths drawn from radiating surface 6 and focus point 18 undergo the same attenuation magnitude.

An added benefit is safety since the power intensity at focal point 18 is the same for all lateral positions of the transducer, in contrast to conventional coupling liquids that do not attenuate. For a water coupling fluid, a An added benefit is safety since the power intensity at focal point 18 is the same for all lateral positions of the transducer, in contrast to conventional coupling liquids that do not attenuate. For a water coupling fluid, very strong signal would occur when the transducer 7 was in the position shown. An added benefit is safety since the power intensity at focal point 18 is the same for all lateral positions of the transducer, in contrast to conventional coupling liquids that do not attenuate. For a water coupling fluid, very strong signal would occur when the transducer 7 was in the position shown. An added benefit is safety since the power intensity at focal point 18 is the same for all lateral positions of the transducer, in contrast to conventional coupling liquids that do not attenuate. For a water coupling fluid, very strong signal would occur when the transducer 7 was in the position shown. An added benefit is safety since the power intensity at focal point 18 is the same for all lateral positions of the transducer, in contrast to conventional coupling liquids that do not attenuate. For a water coupling fluid, very strong signal would occur when the transducer 7 was in the position shown.very strong signal would occur when the transducer 7 was in the position shown.

Part of the purpose of this apparatus is to fair in the natural body shape to create a smooth interface while maintaining quality of focus and apparent sidelobe levels. Comfort to the patient is provided by avoiding direct contact with fluid and avoiding any significant pressures against the body. The vacuum process is benign because the rubber sheet 2 is compliant. The fairing effect of the Mylar sheet 5 means that a larger breast will be slightly pressed down while a smaller breast might not even reach the height of the Mylar sheet 5. In either case, high resolution imaging would be maintained.

The transducer face 6 is shown with curvature that matches a wavefront curvature that will focus at focus point 18. In cases where flat arrays are used and time delay is used to form a wavefront, the attenuation of an attenuating fluid 22 in the upper container 21 will not be correct unless signals from transducer elements are correctly adjusted. This adjustment will vary with different locations of focal point 18 and it is part of the problem of beam steering in general.

The Mylar sheet can be stretched tight over more complicated frames so as to better apply to some body parts. If a frame is rectangular box, open at top and bottom, but two opposite ends of the box are shaped as curved arches, then the stretched Mylar surface will be curved in one dimension and this surface will be like a section of a hollow cylinder. Such design variations are suitable for operation with some transducer designs.

A system design will utilize the methods, forms, and materials described in FIG. 1 as needed for particular applications.

A simplified variation is a hand held form as illustrated in FIG. 2. Here a bladder device made of thin rubber, as specified for the rubber sheet 2 of FIG. 1. This apparatus retains the same reservoir 13 and tube 12 as before. The reservoir elevation would be higher than the bladder device 16 to keep most fluid in the bladder 16. The transducer 7 is now hand held and lateral motions 8 and axial motion 9 are manually carried out. Operation of this arrangement is made flexible because the amount of fluid in the pouch can vary so that contact with the pouch will be maintained for a substantial range of axial motion of the transducer. If electronic system settings are kept unchanged, the image frame can be safely moved in the axial direction as needed and moving across uneven body contours can be safely done.

The hand held method is again illustrated in FIG. 3. Here the reservoir is eliminated and the bladder 16 is filled with attenuating fluid through a rubber plug 17 with a syringe. A particular form is implemented using Hitachi Part Number EZU-WL1 with evaporated milk being the fluid that is inserted with the syringe after any water therein is removed. Use of this device as herein modified will prevent accidental use of high intensity ultrasound when using it with a stand off to see shallow features in the body. It will also assure that all ray paths from the transducer face 6 to the focus point 18 are equally attenuated.

When a conventional ultrasound transducer such as illustrated in FIG. 2 or FIG. 3 is operated with its associated electronic system the appropriate phase and amplitude control of signals is provided such that imaging is effective from near the skin down to a particular depth. With the herein disclosed device the same phase and amplitude control would be maintained so the image frame would be displaced to a shallower range of depths and part of the image frame would thus be in the stand off fluid. This can result in viewing in a more effective part of a frame, it can result in the image frame accommodating irregular body surfaces, and it can enable viewing at angles not perpendicular to the skin. Because water does not attenuate signals like body tissue attenuates signals, image signals are not adequately maintained over the aperture and image quality is degraded.

It is appropriate to provide an ultrasound conducting gel to assure continuous contact with the skin. This is desirable, even with the vacuum system in operation. Where this is a thin layer, it is not necessary that this material be an attenuating material. As operating frequencies increase, it will be necessary to evaluate the degree of surface irregularity and to utilize attenuating gel should attenuation leveling be appropriate.

FIG. 4 illustrates an experimental arrangement that illustrates basic principles of the attenuation leveling method as well as an embodiment of the invented apparatus. A glass tank 31 contains a coupling fluid 32 and a transducer array 33 includes a plurality of vertical elements. A circle 34 is a visualization aid to show how the array elements are arranged to focus at a focus point 39 along a vertical line 38. An abstract body part is depicted by the hemispherical container 37 that is shown as a wire frame model that is enclosed by a thin rubber surface that is the shape of the frame. The body part is called a phantom and it is modeled by filling the container 37 with fluid that acts like breast tissue. The edge ray path 35 travels a shorter part of its route through tissue than does the central ray path 36. By using coupling fluid 32 that attenuates like tissue, both path undergo the same attenuation. An attenuating coupling fluid is formulated utilizing the same recipes that are disclosed for making tissue mimicking phantoms as given in U.S. Pat. No. 5,902,748 (May 1999) Madsen et al. This coupling fluid assures that the wavefront that is initially produced by the array of transducers 33 is correctly maintained as it converges to the focus point 39.

The herein disclosed method and apparatus have utility in any field where attenuation of propagating signals modifies the intensity distribution of signals over the surface of a wavefront and the amplitude of signals over the frequency spectrum.

What is claimed is:

1. A sensing system comprising
   (a) a signal generator that produces wide band transmit signals that have an equivalent representation in a frequency domain that is indicated by a frequency spectrum, and
   (b) a transducer device that converts said wide band transmit signals to wide band wave signals that propagate in a medium as indicated by propagating wavefronts, where said medium is a combination of different materials, where said propagating wavefronts propagate in said medium where said different materials cause different signal attenuation that variably attenuates said wide band wave signals that are distributed over said wavefronts, and
   (c) attenuation leveling material having attenuation that matches attenuation of a subject of examination, and a device to arrange said attenuation leveling material such that said propagating wavefronts propagate through materials having approximately the same attenuation for any single frequency, to cause uniformity in amplitude of said wide band wave signals that are distributed over propagated wavefronts, for said any single frequency, and
   (d) a receiving device that responds to said propagated wavefronts to produce wide band received signals, and
   (d) a signal modification device that modifies said wide band transmit signals to produce pre-compensated signals that compensate for propagation effects such that said wide band received signals are uniform in amplitude over a frequency spectrum.

2. A sensing system according to claim 1 and a vacuum device that improves contact between said conforming surface and said surface of said subject of examination.

3. A sensing system according to claim 1 and a conforming surface to isolate coupling fluid from a surface of a subject of examination, and contact enhancing gel that improves transfer of ultrasonic wave signals between said conforming surface and said surface of said subject of examination.

4. A sensing system according to claim 1 where said attenuation leveling material is an attenuating fluid.

5. A sensing system according to claim 1 where said attenuation leveling material is an attenuating fluid that has low scattering properties.

6. A sensing system according to claim 1 where said attenuation leveling material is an attenuating fluid that magnitude of scattering does not add to an effect of scattering of a tissue type being examined.

7. A sensing system according to claim 1 where said attenuation leveling material is evaporated milk.

8. A sensing system according to claim 1 where said attenuation leveling material is a gel.

9. A sensing system according to claim 1 where said fairing device is a flat Mylar sheet.

10. A sensing system according to claim 1 where said fairing device is a thin sheet of material stretched over a frame so that it is shaped by said frame.

11. A sensing system according to claim 1 where said conforming surface is a thin rubber sheet.

12. A sensing system according to claim 1 where said system is used for breast imaging.

13. A sensing system according to claim 1 where said transducer operates within attenuating fluid.

14. A sensing system according to claim 1 where said transducer scans laterally without variation in operating power levels.

15. An ultrasonic system that includes a transducer and a stand-off pad that couples wave signals between said transducer and a body to be examined, and said stand-off pad being adapted to conform to a surface of said transducer and to conform to a surface of said body to be examined thereby defining conforming surfaces of said pad, where said body to be examined attenuates said wave signals, and said wave signals are defined by successive wavefronts, where signals are distributed over a wavefront, where said standoff pad contains attenuating material having attenuation that approximately matches attenuation of said body to be examined, such that significant uneven attenuation of signals that are distributed over a respective wavefront is prevented, where said system has means such that said transducer produces wave signals that are wideband transmit signals, and said transducer receives signals to produce wideband receive signals, and said wideband transmit signals are pre-compensated to cause said wideband receive signals to be approximately uniform in amplitude over a wide frequency bandwidth.

16. An ultrasonic system according to claim 15 where said pad causes attenuation leveling.

17. An ultrasonic system according to claim 15 where attenuation of said pad enables operation of ultrasonic equipment without power reduction.

18. An ultrasonic system according to claim 15 where said pad contains milk.

19. An ultrasonic system according to claim 15 where said pad contains evaporated milk.

20. An ultrasonic system according to claim 15 where said pad is equipped with a port that enables filling with a syringe.

21. An ultrasonic system according to claim 15 where said pad is connected to a reservoir by a tube so that attenuating fluid can allow volume of said pad to vary.

22. An ultrasonic system according to claim 15 and a vacuum device to assure close contact with a body surface.

23. An ultrasonic system according to claim 15 and an ultrasonic transducer device that is operated at an angle not perpendicular to skin surface of a body to be examined.

24. An ultrasonic system according to claim 15 and an ultrasonic transducer device that is operated in relation to uneven body surfaces.

25. An ultrasonic system according to claim 15 and medical operations that produce images of tissue within a body that is being examined.

26. An ultrasonic system according to claim 15 and coupling gel that improves signal transfer.

27. An ultrasonic system according to claim 15 where said pad is a container made of thin rubber that is a conforming surface.

28. An ultrasonic system according to claim 15 and a device to inject a substance into a subject of examination.

29. An ultrasonic system according to claim 15 and apparatus to guide surgical instruments.

30. An ultrasonic system according to claim 15 and apparatus to guide injection instruments.

31. An ultrasonic system according to claim 15 where said pad is a firm gel.

32. An ultrasonic system according to claim 15 where said pad is an attenuating gel having sufficient viscosity that it remains between a transducer and skin of a subject.

33. A sensing system for examining a subject, said sensing system comprising
   (a) a transducer apparatus that operates in relation to wavefronts in a medium of propagation, where said medium includes material that is included in said subject, where said medium causes frequency dependent attenuation, and
   (b) signal modification apparatus that compensates for said frequency dependent attenuation to produce compensated signals, where said compensated signals include frequency component signals that are distributed over a frequency spectrum, where compensation includes adjustments at component signal frequencies that offset attenuation effects at respective operating frequencies to control relative amplitude of respective said frequency component signals.

34. A system according to claim 33 where said compensation for frequency dependent attenuation is compensation that is accomplished by modifying received signals.

35. A system according to claim 33 where said compensation for frequency dependent attenuation is compensation that is accomplished by modifying transmit signals.

36. A system according to claim 33 where said medium includes a coupling material that enables propagation between said transducer apparatus and said subject, where said coupling material is held between said transducer apparatus and said subject, and said coupling material is an attenuation leveling material that is selected such that attenuation effects at operating frequencies in said attenuation leveling material match attenuation effects at respective operating frequencies in said subject to enable control of signal amplitude for signals that are distributed over a wavefront.

* * * * *